US00RE39396E

(19) United States
(12) Reissued Patent
Swift et al.

(10) Patent Number: US RE39,396 E
(45) Date of Reissued Patent: Nov. 14, 2006

(54) MOBILE X-RAY INSPECTION SYSTEM FOR LARGE OBJECTS

(75) Inventors: Roderick Swift, Belmont, MA (US); Andrew Tybinkowski, Boxford, MA (US)

(73) Assignee: American Science and Engineering, Inc., Billerica, MA (US)

(21) Appl. No.: 10/229,993

(22) Filed: Aug. 28, 2002

Related U.S. Patent Documents

Reissue of:
(64) Patent No.: 6,252,929
Issued: Jun. 26, 2001
Appl. No.: 09/305,417
Filed: May 5, 1999

U.S. Applications:
(63) Continuation of application No. 09/072,212, filed on May 4, 1998, now Pat. No. 5,903,623, which is a continuation of application No. 08/799,533, filed on Feb. 12, 1997, now Pat. No. 5,764,683
(60) Provisional application No. 60/011,495, filed on Feb. 12, 1996.

(51) Int. Cl.
*G01N 23/04* (2006.01)

(52) U.S. Cl. ..... 378/57; 378/86
(58) Field of Classification Search ..... 379/57, 379/86–88
See application file for complete search history.

(56) References Cited

U.S. PATENT DOCUMENTS 3,569,708 A * 3/1971 Weinbaum et al. ..... 378/90
3,868,506 A * 2/1975 Ogiso ..... 378/72
RE28,544 E * 9/1975 Stein et al. ..... 378/146
3,928,765 A * 12/1975 Teller ..... 378/53
4,047,029 A * 9/1977 Allport ..... 378/90
4,052,617 A * 10/1977 Garrett et al. ..... 378/55
4,342,914 A * 8/1982 Bjorkholm ..... 378/113
4,768,214 A * 8/1988 Bjorkholm ..... 378/87
4,799,247 A * 1/1989 Annis et al. ..... 378/87
4,864,142 A * 9/1989 Gomberg ..... 250/390.04
4,884,289 A * 11/1989 Glockmann et al. ..... 378/57
4,974,247 A * 11/1990 Friddell ..... 378/90
5,014,293 A * 5/1991 Boyd et al. ..... 378/197
5,022,062 A * 6/1991 Annis ..... 378/86
5,065,418 A * 11/1991 Bermbach et al. ..... 378/57
5,132,995 A * 7/1992 Stein ..... 378/56
5,181,234 A * 1/1993 Smith ..... 378/87
5,224,144 A * 6/1993 Annis ..... 378/146
5,253,283 A * 10/1993 Annis et al. ..... 378/98.7
5,302,817 A * 4/1994 Yokota et al. ..... 250/214 VT
5,313,511 A * 5/1994 Annis et al. ..... 378/87
5,638,420 A * 6/1997 Armistead ..... 378/57
5,692,028 A * 11/1997 Geus et al. ..... 378/57
5,692,029 A * 11/1997 Husseiny et al. ..... 378/88
5,764,683 A * 6/1998 Swift et al. ..... 378/57
5,903,623 A * 5/1999 Swift et al. ..... 378/57

* cited by examiner

*Primary Examiner*—Craig E. Church
(74) *Attorney, Agent, or Firm*—Bromberg & Sunstein LLP

(57) ABSTRACT

A device for inspecting a cargo container such as a motor vehicle or freight pallet, with penetrating radiation. A source of penetrating radiation is mounted on a moveable bed, thereby allowing a beam of penetrating radiation to sweep the large container. At least one detector is also mounted on the bed, either on the side of the source or on a boom, so that, as the beam is scanned across the container, the container and any contents of the container are characterized by transmitted or scattered radiation, or both.

14 Claims, 5 Drawing Sheets

MOBILE X-RAY INSPECTION SYSTEM FOR LARGE OBJECTS

Matter enclosed in heavy brackets [ ] appears in the original patent but forms no part of this reissue specification; matter printed in italics indicates the additions made by reissue.

The present application is a continuation of U.S. patent application Ser. No. 09/072,212, filed May 4, 1998, now U.S. Pat. No. 5,903,623 currently allowed, itself a continuation of Ser. No. 08/799,533, filed Feb. 12, 1997, issued as U.S. Pat. No. 5,764,683, all of which are incorporated herein by reference. The present application claims priority from U.S. provisional application No. 60/011,495, filed Feb. 12, 1996, also incorporated herein by reference.

The U.S. Government may have a paid-up license in portions of this invention and the right in limited circumstances to require the patent owner to license others on reasonable term as provided by the terms of Contract No. N39998-97-C-5209 awarded by the U.S. Department of the Navy, and Grant No. 93-G-003 awarded by the U.S. Department of Transportation Federal Aviation Administration.

FIELD OF THE INVENTION

The present invention relates to the inspection of large containers by means of x-ray radiation, and more particularly to the x-ray inspection of cargo containers by means of transmitted and back, scattered radiation.

BACKGROUND ART

The interdiction of illicit drugs, explosives, and other contraband is an important goal of law enforcement. To that end, a variety of technologies have been developed and deployed for the non-intrusive inspection of containers not readily susceptible to visual scrutiny from the outside. The non-intrusive aspect of these inspection techniques is important; the great majority of containers do not carry contraband, and the public would not long tolerate the delays, disruption (and in some cases damage) of property, and invasions of privacy that would occur if invasive inspection means were commonly used. Non-intrusive inspection is typically nondestructive and can usually be accomplished faster than intrusive inspection, hereby increasing productivity of inspectors. Increased productivity means more containers inspected and mor contraband interdicted.

Among non-intrusive inspection methods, x-ray imaging in its many forms has been a proven technology capable of detecting a variety of contraband. X-ray systems have been based on transmission imaging in any of a variety of implementations; cone-beam (fluoroscopes), fanbeam, flying-spot, multi-projection configurations; dual-energy imaging; computed tomography; as well as on imaging incorporating the detection of x-ray radiation scattered in various directions.

With only a few exceptions, x-ray imaging systems for contraband detection have operated within the source-energy range of 70 keV to 160 keV. Since the penetrating power of these sources is limited, inspection is limited to relatively small parcels and containers. A few large, expensive, high-energy transmission imaging systems have also been built for the inspection of large containers or vehicles. These systems typically operate within the range of 6 MeV to 12 MeV, require heavily-shielded, fixed installations, and provide no means to distinguish organic materials.

Radiant energy imaging with a scanning pencil beam is the subject of U.S. Pat. No. 3,780,291. The creation and we of images from scattered x-radiation in conjunction with direct transmission images is the subject of U.S. Pat. No. 5,313,511. These patents are hereby incorporated herein by reference. Neither of the foregoing references, our any prior an known to the inventors herein, discloses or suggests how x-ray images, in a sense defined below, may be formed of cargo containers on the scale of mow, vehicles or railroad cars using a source of penetrating radiation and detectors mounted on a mobile platform.

SUMMARY OF THE INVENTION

The current invention extends the role of inspection by penetrating radiation to encompass large containers and over-the-road vehicles, and at the same time retains the advantages of discriminating among materials as provided by backward, forward, or sideward scatter imaging.

In a preferred embodiment, the invention provides a device for inspecting a cargo container with penetrating radiation. The device of (his embodiment has a bed moveable along a first direction having a horizontal component, a source of penetrating radiation, mounted on the bed, for providing a beam, a motorized drive for moving the bed in the first direction, and at least one detector mounted on the bed and having a signal output so that the beam is caused to traverse the cargo container as the bed is moved and each detector provides a signal for characterizing the cargo container and any contents of the cargo container. In further embodiments of the invention, the source of penetrating radiation may be an x-ray source, and the at least one detector may be a backscatter detector, a transmission detector, a sidescatter detector, or a forward scatter detector. The beam may be a pencil beam scanned repeatedly along a second threaten having a vertical component.

In a further embodiment, the device also has a boom, movably linked to the bed. The boom has a storage position, substantially fixed with respect to the bed, and an operation position that is transverse to the first direction, as well as an end region. Abeam catcher is attached to the end region of the boom for impeding the further passage of penetrating radiation in the second direction when the boom is in the operation position. The back scatter detector has upper and lower elements, the upper element being movably mounted with respect to the lower element, so that in a first position the upper element is transversely disposed with respect to the lower element and in a second position the upper element is substantially collinear with respect to the lower element. The source of penetrating radiation may provide a pencil beam that is scanned repeatedly over an angle of regard, the angle having an orientation with respect to the horizontal, and the device also includes a steering arrangement for steering the orientation of the angle of regard with respect to the horizontal.

Instead of fitting the boom with a beam catcher, the boom may be alternatively provided, at its end region, with a transmission detector attached to respond to penetrating radiation transmitted through the container, so as to provide a signal for forming a transmission image of the container. In further embodiments, the source of penetrating radiation includes an x-ray rube operating at a voltage in substantial excess of 200 kV, and may operate in a region of approximately 450 kV.

In a further embodiment, the invention provides a method, for producing an x-ray image of a large object, utilizing a device such as described above, along with an arrangement for processing the signal from the signal output of the detector to form an image of the object.

In a further embodiment, the invention is a scatter image of an object. The image is formed by (a) providing a device such as described above, then (b) using the motorized drive to move the device past an object so as to cause the object to be scanned along two dimensions; and (c) processing the signal From the signal output of the detector to form an image of the object. The object may, for example, be a motor vehicle having at least two pairs of wheels. The object may also, for example, be a trailer, a railroad car, a sea cargo container, an air cargo container, or a freight pallet.

BRIEF DESCRIPTION OF THE DRAWINGS

The invention will more readily be understood by reference to the following description taken with the accompanying drawings, in which.

DETAILED DESCRIPTION OF SPECIFIC EMBODIMENTS

As used in this description and in the appended claims, a "cargo container" is a receptacle for the storage or transportation of goods, and includes freight pallets as well as vehicles, whether motorized or drawn, such as automobiles, the cab and trailer of a truck, railroad cars or ship-borne containers. The term "cargo container," as used herein, further includes the structures and components of the receptacle.

The invention described herein serves to characterize materials which may be contained within a cargo container and thus not readily susceptible to visual scrutiny. The characteristics of a material which might be the object of non-invasive inspection and which lend themselves to detection using the device and method taught by the invention include, but are not limited to, electron density, atomic number, mass density, linear dimensions and shape. These characteristics are unveiled by taking advantage of the various physical processes by which penetrating radiation interacts with matter. Penetrating radiation refers to electromagnetic radiation of sufficient energy per photon to penetrate materials of interest to a substantial and useful degree and include x-rays and more energetic farms of radiation. The interaction of such radiation with matter can generally be categorized as either scattering or absorption processes. Both types of process remove x-ray photons from a collimated (i.e., directional) beam; scattering processes do so by deflecting photons none new directions (usually with loss of energy), while absorption processes simply remove photons from the beam.

Conventional transmission imaging measures the total beam attenuation as a function of position on the image plane, without discriminating between absorption and scattering processes. The total beam attenuation is described by a parameter called the term attenuation coefficient, as commonly employed by persons skilled in the art of x-ray inspection. The mass attenuation coefficient is a characteristic of a particular material at a specific x-ray photon energy, and is independent of the imaging geometry. As such, it is the sum of individual coefficients (or "cross sections") for each relevant physical process, each of which varies differently with x-ray energy and with the atomic number (Z) of the interacting material.

Figure 1:
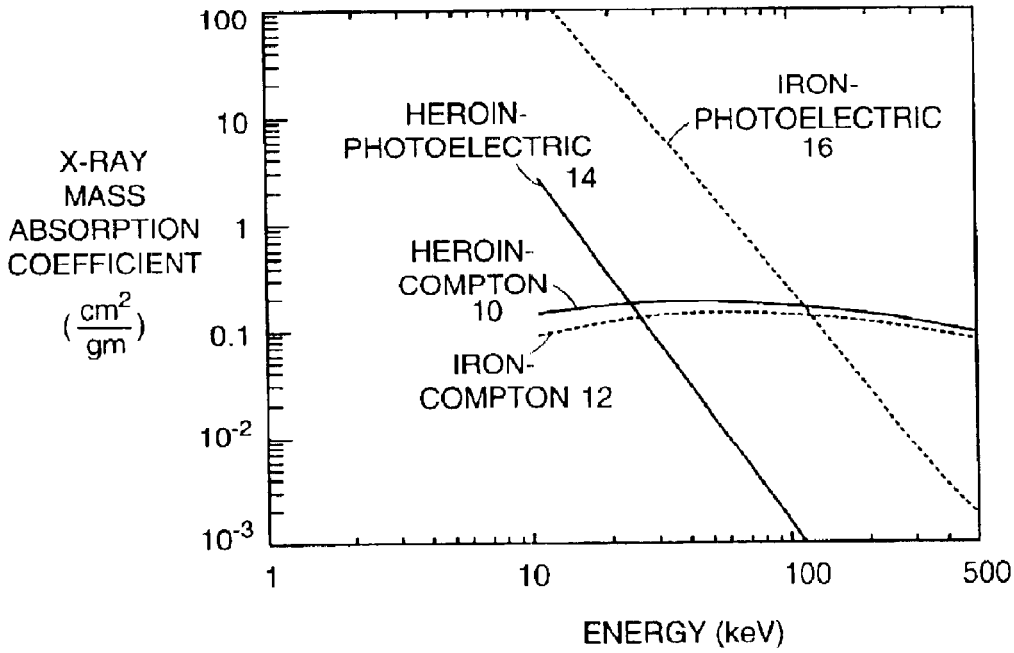
FIG. 1 is a plot of the x-ray interaction coefficients of two materials, heroin and iron, over the range of x-ray photon energies from 10 to 500 keV.

In the range of photon energies useful for penetrating and screening cargo containers, the scattering contribution is dominated by incoherent, or Compton scattering and the absorption contribution is dominated by the photoelectric effect. The cross sections for Compton scattering and photoelectric absorption vary with both the atomic number of the material and with the energy of the x-ray photon, but in very different ways. The photoelectric absorption decreases very rapidly with increasing photon energy, and increases very rapidly with increasing Z of the material. The Compton scattering cross section changes very slowly with energy and is only weakly dependent on atomic number. These functional relationships are illustrated in FIG. 1 for two relevant materials (iron and heroin). The Compton scattering cross section 10 for a low-Z material such as heroin and the Compton scattering cross section 12 for iron are nearly identical over the energy range of interest, and show little variation with energy. However, the photoelectric cross sections 14 and 16 are very different for the two materials, and both vary rapidly with energy. For heroin, the Compton scattering cross section 10 dominates the photoelectric cross section 14 for all x-ray energies above 20 keV. In contrast, for iron the photoelectric cross section 16 dominates for energies up to about 120 keV. Over the range from 60 keV to 400 keV, the total absorption coefficient (the sum of the Compton and the photoelectric coefficients) varies by less than a factor of two for heroin but by about a factor of 13 for iron. Such differences in scattering and absorption characteristics between low Z materials, characteristic of organic materials, and high Z materials, characteristic of most metals and their alloys, are typical and provide the means to differentiate between these two classes of materials.

Conventional transmission x-ray images-simply provide a map of the attenuation characteristics of the inspected object for the full spectrum of the x-ray beam. It should be noted that images may be directly displayed in graphic format for the visual inspection of human operators, but need not be so displayed. As used in this description and in the appended claims, the term "image" refers to any multidimensional representation, whether in tangible or otherwise perceptible form or otherwise, whereby a value of some characteristic is associated with each of a plurality of locations corresponding to dimensional coordinates of an object in physical space, though not necessarily mapped one-to-one thereonto. Thus, for example, the graphic display of the spatial distribution of some feature, such as atomic number, in one or more colors constitutes an image. So, also, does an array of numbers in a computer memory or holographic medium. Similarly, "imaging" refers to the rendering of a stated physical characteristic in terms of one or more images.

Backscatter imaging in which the x-rays scattered by a material in a generally backward direction are employed offers several unique inspection capabilities and operational features. (1) Taken alone, it is a one-sided imaging modality: images can be obtained even when the object is accessible from only one side, or, the object is too thick to be penetrated radiographically. (2) Because the scatter signal falls off quite rapidly with increasing depth into the object, backscatter images effectively represent a "slice" of the object characteristic of the side nearest to the x-ray source; this image is frequently useful even when a transmission image representing the same scanned area is hopelessly confused by image clutter. (3) The underlying physical phenomenon that leads to scattered radiation is the Compton effect. Low atomic number (low Z) materials, which encompass organic materials, interact with x-rays principally by Compton scattering. Narcotic drugs, being among the densest of organic materials, tend to produce the brightest signatures in a backscatter image, as do organic explosives, making backscatter imaging a useful imaging modality for bomb or drug detection. (4) Alignment requirements of the x-ray beam with detectors or collimation devices are less exacting than for transmission imaging thereby enabling rapid deployment in a wide range of inspection scenarios.

To the extent that Compton scattering removes x-ray photons from the x-ray beam, it contributes to the attenuation map image produced by transmitted x-rays. However, a scattered photon that is removed from out beam path projection and scattered into another contributes only an unwanted background or "fog" in the transmitted x-ray image. In cone-beam imaging geometries (e.g., film radiography), the scattered background can be a serious problem, and can, in fact, dominate over the transmitted x-ray image data.

It is known in persons skilled in the art of x-ray inspection that high-Z and low-Z materials may be separately identified by measuring total attenuation at two different photon energies. This is the basis for the dual-energy systems in widespread use for airport baggage inspection.

Another method to image low-Z materials is backscatter imaging. The technique relics upon the direct detection of photons which have been Compton scattered. An image is created that is separate and independent of any transmission image that may be produced at the same time. Since the photoelectric absorption cross section is small for organic materials, they interact almost entirely through Compton scattering, producing relatively large scatter signatures. Metals, on the other hand, interact almost exclusively by photoelectric absorption, an that their scatter image signature is comparatively small. The backscatter image directly reveals organic materials such as drugs or explosives.

Flying-spot technology makes possible the acquisition of images using detectors specifically positioned to collect the scattered x-rays. In a typical flying-spot system, a thin "pencil beam" of x-rays is rapidly and repetitively swept through a source-centered, vertically-oriented "fan" of beam paths that are arranged to intercept the object under inspection. At the same time, the object is moved at a constant, slower speed along a path perpendicular to the fan, on a horizontally moving conveyer belt for example. In this way, the pencil beam is made to traverse the object in point-by-point raster fashion, and the entire object is scanned as it passes through the fan plane over a period ranging from a few seconds to a few minutes depending upon the length of the object.

Although the total scan time is seconds to minutes in duration, the actual exposure time of any part of the scanned object is only the time it takes for the pencil beam to sweep across that pixel. That exposure time is typically in the range of 8 to 64 microseconds, depending on the design and the application, and yields an entrance exposure to the scanned object of only tens or hundreds of microroentgens. This low dose to the object also means that there is little radiation available to scatter into the environment, so the doses to operators and other bystanders is correspondingly low. Separate, large-area detectors are deployed adjacent to the beam plane on the x-ray source side of the scanned object, and with their active surfaces oriented toward the scanned object. These detectors need only provide a large solid angle for collection of scattered radiation; no critical alignments are required. In this location these detectors respond to x-rays which are scattered generally back toward the source from the object.

Typically, the transmission x-ray signature of organic materials is relatively weak in comparison to that of higher density, higher atomic-number materials such as metals. Since the x-ray transmission image is a result of interactions throughout a path through the entire object, larger and more complex objects such as cargo containers produce more confusing transmission images. Under these circumstances, even the presence of small amounts of metal and normal expected organic materials can produce extremely cluttered images masking the sought-for contraband. Image interpretation then becomes an overwhelming task. Frequently, most of the useful information is obtained from the backscatter image alone.

In a preferred embodiment of the present invention, the cargo container inspection device time flying-spot x-ray imaging and backscatter imaging technologies. Equipment costs can be reduced if backscatter imaging is used to the exclusion of other modes of x-ray interrogation of the contents of the cargo container.

Figure 2A:
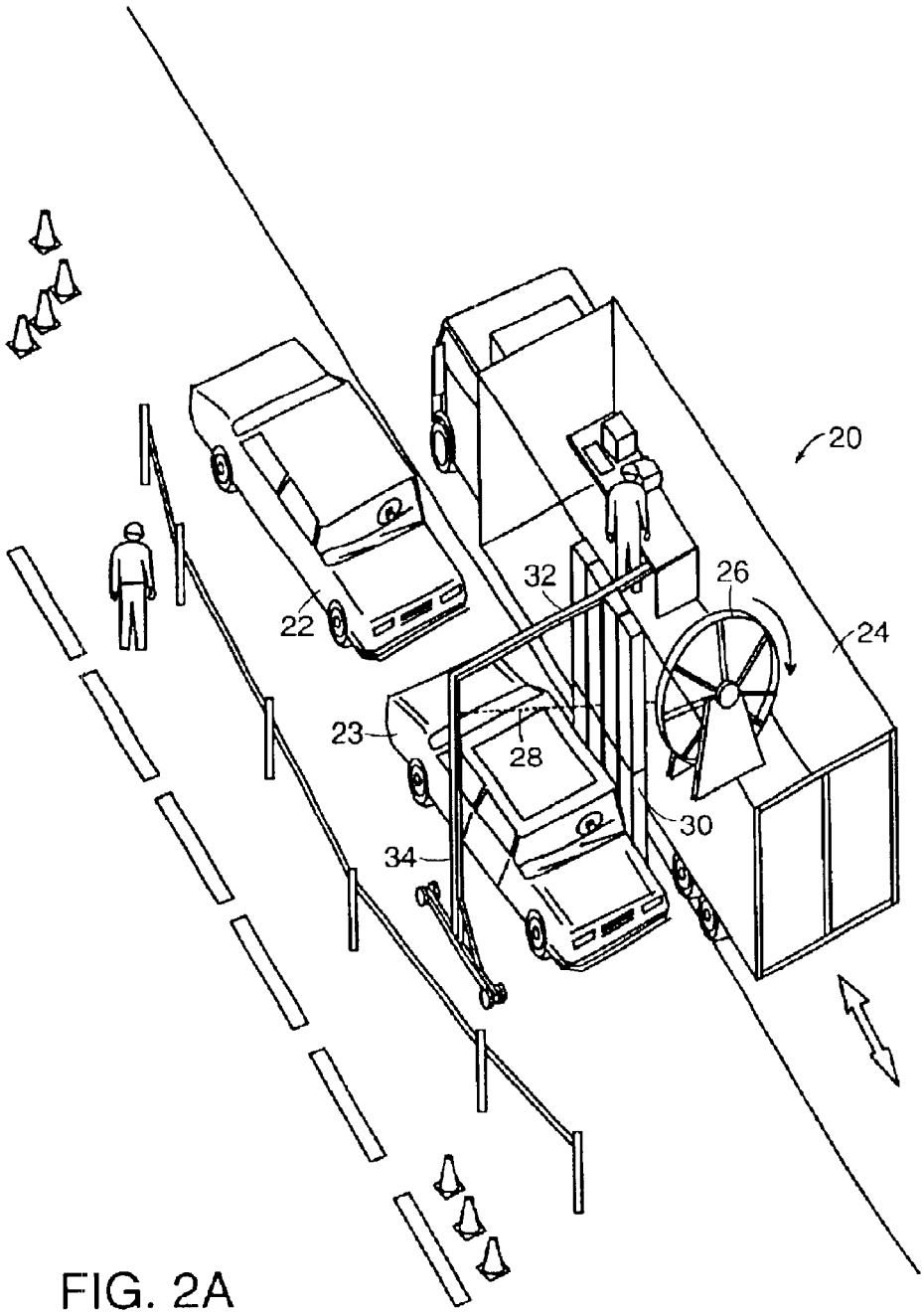
FIG. 2A is a perspective view of a device for inspecting a large container with penetrating radiation in accordance with a preferred embodiment of the invention.
Figure 2B:
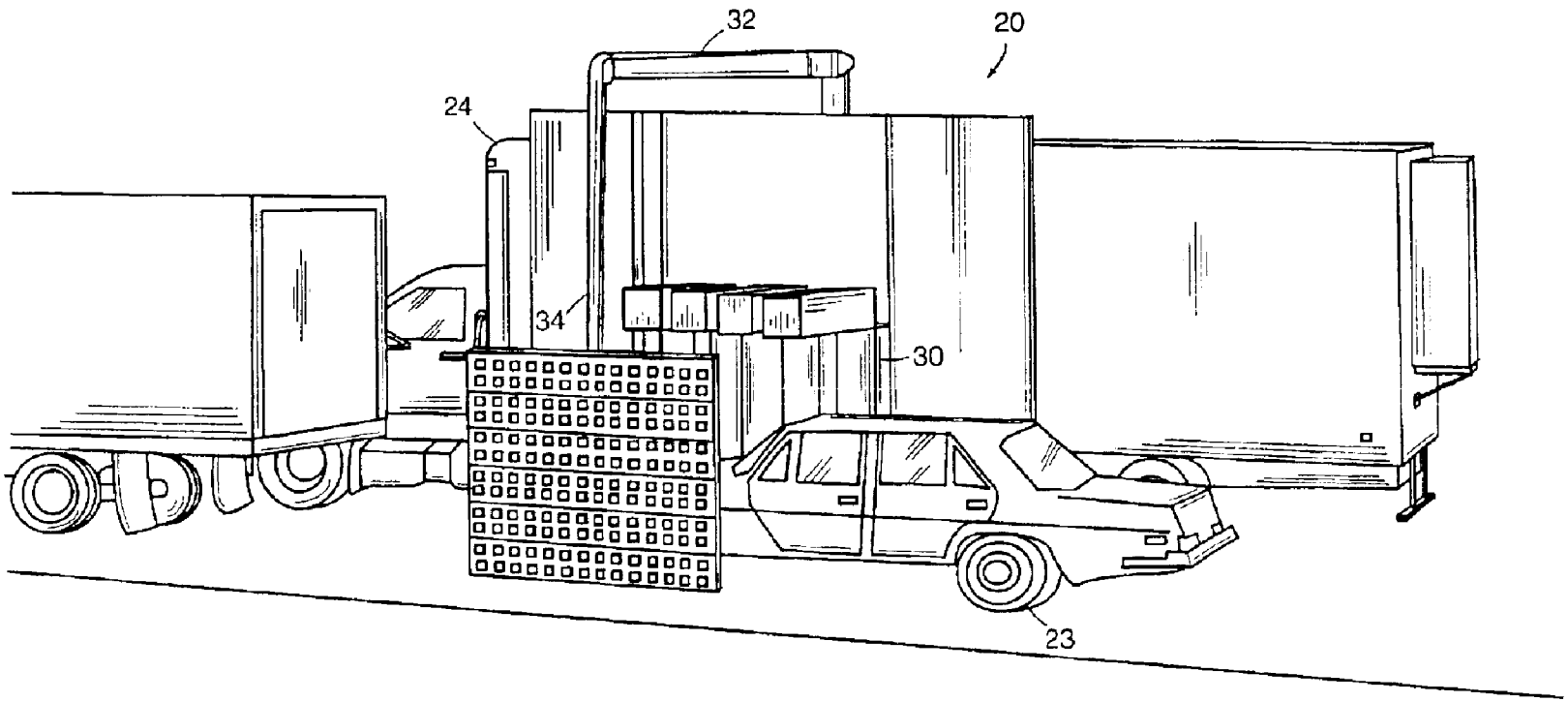
FIG. 2B is aside view of a further embodiment of a device for inspecting a large container with penetrating radiation in accordance with the invention.

Referring now to FIG. 2A, a perspective view is shown of a cargo container inspection system, designated generally by numeral 20, in accordance with a preferred embodiment of the invention. Cargo container inspection system 20 is shown deployed for inspection of passenger cars 22 and 23. FIG. 2B shows a preferred embodiment of the invention. With reference to FIGS. 2A and 2B, a truck 24, typically 35' Long×8' wide×10'6" high, houses and supports the x-ray inspection equipment, ancillary support and analysis systems, and a hydraulic slow-speed drive mechanism to provide the scan motion. Truck 24 serves as both the platform on which the mobile system is transported to its intended operating site, and a bi-directional translation stage, otherwise referred wherein as a "bed,"to produce the relative motion required during a scan. Chopper 26 is used, in accordance with flying spot generation techniques known to persons skilled in the art, to scan beam 28 of penetrating radiation recursively in a vertical direction. Radiation scattered by the contents of the cargo container, shown here as passenger car 23, is detected by x-ray backscatter detectors 30. Boom 32 allows beam stop 34 to track beam 28 as truck 24 advances in scanning past the cargo container. Beam stop 34 is also referred to as a "beam catcher." In addition or alternatively to beam stop 34, an x-ray transmission detector may be mounted in opposition to beam 28, tracking beam 28 on the distal side of the sunned cargo container.

Figure 3:
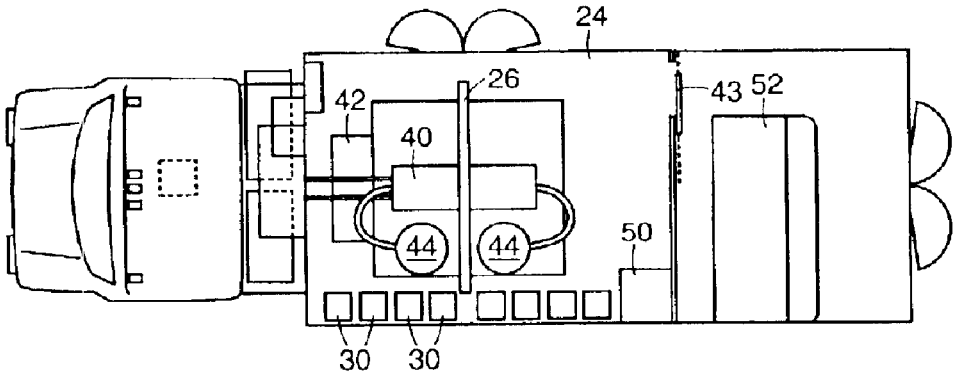
FIG. 3 is a top schematic view of the layout of the system shown in FIG. 2B, as configured for transport.
Figure 4:
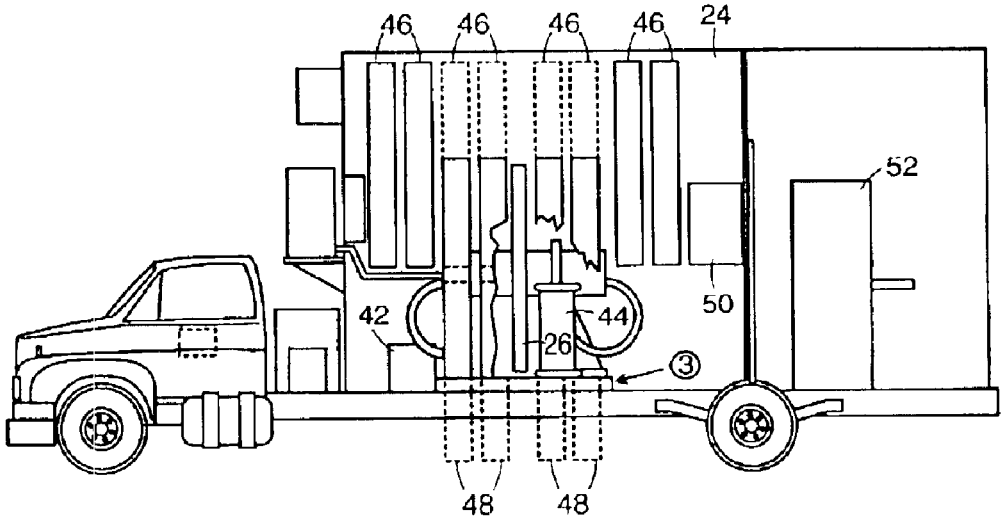
FIG. 4 is a side elevation schematic view of the layout of the system shown in FIG. 2B.

Referring now in FIG. 3, a top schematic view of the layout of the system shown in FIG. 28, is depicted as configured for transport. FIG. 4 is the corresponding side elevation, additionally showing the detectors in one of two available deployed positions. The module components comprising the cargo container inspection system are: the penetrating radiation source assembly 40; x-ray high voltage generating subsystem including high voltage power supply 42 and high voltage tanks 44; backscatter detector modules 30, comprised of an upper bank 46 of detectors add a lower bank 48 of detectors; detector electronics module 30; and operator's console 52. The dashed position of upper backscatter detector banks 45 indicate the position for inspection of cargo containers. The x-ray source 40, high-voltage power supply 42, and positive and negative high-voltage tanks 44, are all in accordance with ordinary practice in the art of x-ray generation. In a preferred embodiment of the invention, a 450 kV x-ray tube is employed.

Figure 5A:
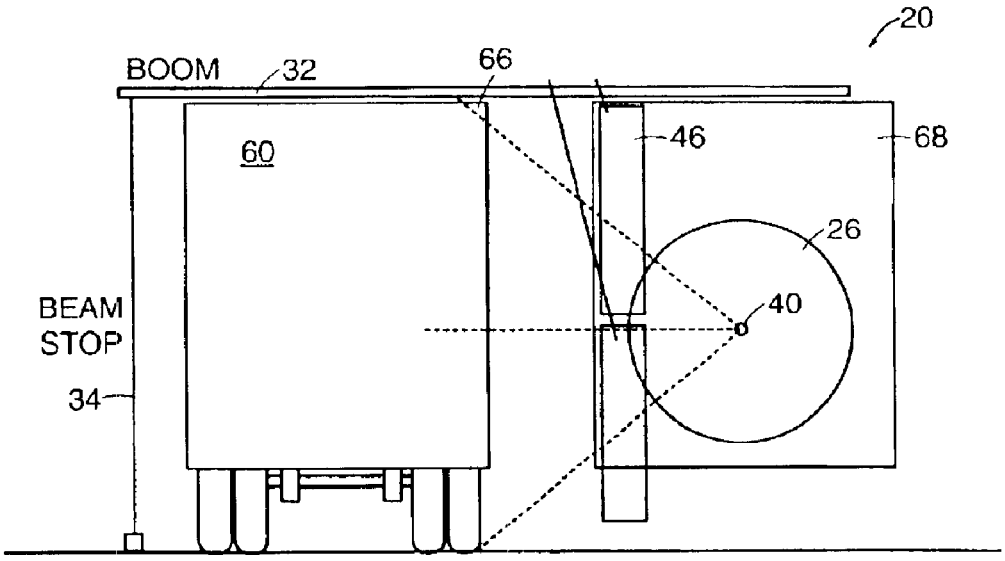
FIG. 5A shows the cargo container inspection system of FIG. 2B, as deployed for inspection of a full-sized tractor-trailer.
Figure 5B:
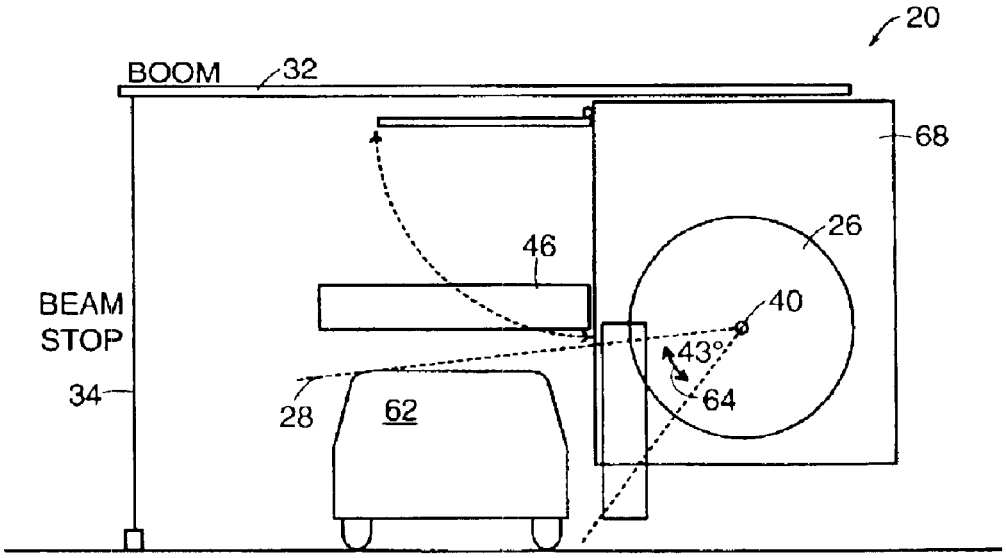
FIG. 5B shows the cargo container inspection system of FIG. 2B, as deployed for inspection of a passenger van.

FIG. 5A shows a cargo container inspection system 20, in accordance with a preferred embodiment of the invention, as deployed for inspection of a full-sized tractor-trailer 60 while FIG. 5B shows the same cargo container inspection system 20 deployed for inspection of a passenger van 62. The angle of elevation 64 of the 43° scanning beam can be changed depending upon the application. For optimum versatility, the range of limiting angles extends from at least 55° below horizontal to 55° above horizontal. This corresponds to an angular adjustment of the source axis from −33.5° to +33.5°.

Operationally, one side of a large truck 60 (up to 14' height), as depicted in FIG. 5A, can be completely covered in three passes; however, in many cases, satisfactory coverage can be achieved in two passes. The system operators must choose between doing a third pass or tolerating a small amount of comer cutoff 66, in which case, higher inspection throughput can he achieved. Since the scanning system is bi-directional, alternate passes can be in the forward and reverse directions.

Operationally, one-side of passengers cars and small trucks is scanned ins single pass of the system. Depending upon the situation, it may be necessary to scan the opposite side as well. The upper set 46 of backscatter detectors can be deployed over the top of smaller vehicles as shown in FIG. 5B, substantially improving the scatter collection efficiency and producing higher quality images. Backscatter detector modules 46 and 48, two are typically 6' long and 1' wide, and each typically comprises four segments.

In a preferred embodiment of the invention, the cargo container inspection system has two scan-speed modes: nominally 3 inches/sec and 6 inches/sec. The faster speed results in higher throughput, the slower mode—higher image quality. In accordance with one embodiment of the invention, image data in either mode is acquired into a 1024×4096×12 bit image memory and displayed onto a 1024×1024 high-resolution display via a continuously-adjustable 12-bit-to-8-bit look-up table. Additional displays can be provided to allow simultaneous viewing of more than one image, or, alternatively, images may be superposed or combined, as known to persons skilled in the art.

Backscatter detectors are mounted to allow efficient collection of scattered radiation from close to the road surface, all the way to the roof of the inspected container. A motorized mechanism enables the upper set of defectors to be deployed over a small vehicle, as shown in FIG. 5B, though other means of deployment are readily apparent to persons skilled in the mechanical arts and are within the scope of the invention.

The operator's console 52 (shown in FIG. 3), provides for the console operator to control the x-ray system and display images. Various display monitors may be provided. One preferred embodiment has an upper display for transmission images, and a lower display for the corresponding backscatter image. Similarly, various display functions may be provided:

Zoom, pan and scroll—Joystick controls allow the operator to display any part of the image at 2× and tax magnifications.

Continuous density expand—This contrast-enhancing feature allows the operator to display any contiguous subset of the 12-bits (4096 digital intensity levels) of image data over the full black-to-white range of grey levels on the display monitors. The implementation is through a set of 10 pin-set push buttons, along with a trackball for fine-tuning.

Edge enhancement—A mathematical algorithm sharpens the image and extends the effective dynamic range of the display for faster and easier image analysis.

Reverse video—Operators may select between positive (black-on-white) or negative (while-on-black) image display, depending on personal preference.

Image archiving—operators may "mark and annotate" the images from the console keyboard, and store them on optical disk for future recall.

Thick 24 containing cargo container inspection system 20 is fitted with a custom-built box (or truck body) 68 (shown in FIGS. 5A and 5B) specified 1o accommodate the imaging equipment, and to provide support structures, environmental control, and electrical power distribution.

Truck 24 is provided with both front- and rear-wheel drive: Standard rear-wheel drive from the truck's engine is used for normal over-the-road navel. An alternative drive mode is powered by a low-RPM hydraulic motor to obtain the very low speeds employed for the scan. The two drives are connected via a switchable gearbox to preclude the possibility of having both active at the same time. The hydraulic motor controls, including speed selection, drive direction, and motion start/stop, are located in the cab of the truck under the control of the driver. As an additional safety feature, actuation of the truck's brake will automatically cause disengagement of the hydraulic clutch. A similar arrangement using a hydraulically-powered front or rear wheel drive is known in the art for other special applications requiring very slow vehicle motion.

Deployable beam stop 34 is employed to assure compliance with FDA radiation safely requirements. However, the output radiation of the system is so low that the health and safety requirements for lose radiation levels is met only a few feet away from the source even if no beam stop is used. Beam stop 34 uses a dense shielding material such as lead that is deployed from the end of a boom 32 that extends about 14' from the side of truck 24 at the location of the x-ray beam 28. Generation of x-rays is prevented by interlock circuits unless boom 32 and beam stop 34 are properly deployed, To stow the beam stop for road travel, the beam stop is retracted into the hollow boom 32. Boom 32 is then rotated parallel to the truck axis and lowered into a cradle in truck box 68.

The scan motion is exceedingly slow −⅓ to ⅕ of a mile per hour. An audible alarm is actuated whenever the scan drive mechanism is engaged for motion in either direction. Since this motion also coincides with x-ray generation, the audible warning also provides an "X-RAYS ON" warning. The x-ray high voltage power supply 42 is interlocked so that it cannot be energized unless both chopper wheel 26 is up to speed and truck 24 is in motion. This additional safety precaution ensures that the scanning beam will not be stationary over any one region of space for a long time, thus ensuring low delivered dose.

Operation will be described as it applies to the inspection of one or more passenger cars; scanning of large vehicles will be similar, except that the upper detectors do not need to be swung outboard in this case. It will also be assumed that the system will first be set up, and that vehicles to be scanned will then be brought to it. An alternative whereby the system is deployed beside parked vehicles or containers calls for a minor variation of procedures.

Upon arrival at the intended inspection site, the operators will first assure that the site is suitable; i.e., that there is a sufficient space available for system operation and that operating space can reasonably be secured for safe operations. They will then position the truck at the starting position for the first scan, assuring that there is sufficient room to move the truck ahead for the required scan distance, usually about 65 feet. (Scans will normally alternate, forward and back; it is also possible to scan sequentially in the forward direction only, to scan a continuous line of parked vehicles for example, provided that the necessary space is free.) Once positioned, the on-board generator is started to provide power for system operation, lighting, and a cooling unit. Operators console 52 is powered up at this time.

The operators then manually deploy the backscatter detectors and the beam stop using a motorized mechanism provided for that purpose. Only the upper set of detectors 46 deploy, as shown in FIG. 5E. The beam stop is deployed by rotating the boom into a position orthogonal to the truck, and then lowering the beam stop out of the boom to its preset limit. This action closes an interlock circuit that is required before x-ray generation is possible. An x-ray lobe warm-up sequence, if necessary, is then initiated from operator console 52.

Following warmup, the physical configuration of the system setup is completed by rotating the x-ray beam angle to the direction (elevation) required for the intended scan operations. This is done by a manually-actuated electric motor, and with the aid of an indicator gauge to assist in setting the desired scan elevation. Scanning operations can then commence.

Scan operations are simple and straightforward. One or mote vehicles are directed to positions along the scan path (up to 65 feet of total vehicle length may be imaged in a single scan) and the drivers and passengers exit the vehicles.

Using menu-driven software, the system's computer is readied for image acquisition. This places the computer and data acquisition electronics into a slates wherein c-rays will be initiated and image acquisition started upon receipt of a "scan" command initiated by the system's slow-speed drive controls. The computer also transmits a "ready" status signal to the scan drive control located next to the driver of truck 24.

The driver sets the desired scan speed and direction at the scan drive control. After the "ready" status is received from the computer, the driver starts the scan by pushing a "start" button and releasing the truck brakes. "Start" initiates motion via the slow-speed drive. The driver has continuous control over the truck. He is responsible for steering, and may stop the truck at any time by actuating the brake. Otherwise, the scan will stop automatically after a full data set has been acquired by the computer (and the "ready" status is removed).

As soon as the truck is in motion, a "scan' signal is sent to the computer. The computer then triggers the x-ray generator to ramp up to its preset operating conditions, and upon confirmation that they have been reached (about 5 seconds later) it starts data acquisition. Data acquisition continues until either the "scan" command is interrupted or the image memory is full.

To break the system down for transportation, electronic systems are shut down and the beam stop and detector mechanisms are retracted and secured for travel. The hydraulic drive is disengaged and its power shut off. The generator is switched off.

In a further embodiment, preferred in various applications, the intensity of the transmitted x-ray beam may be measured by a single, elongated transmission detector located on the opposite side of the inspected object from the x-ray source and carefully aligned with the plane of the x-ray beam. The detector is designed to accept and respond to x-rays striking anywhere along the length of its linear entrance slit. The detector is oriented so that the flying-spot beam sweeps repetitively from end-to-end along the slit while truck 24 moves past the inspected object. The detected signal is amplified, integrated, sampled and digitized into an image memory over many sequential, short time intervals during each sweep of the pencil beam. Each such digitized sample forms one pixel of the final image, and the series of samples acquired during one sweep of the beam constitutes one line of image data-typically 1024 samples per line. A complete image frame is constructed by acquiring successive lines as the abject is moved through the scan plane.

In the flying beam mode, the positional image information is acquired by correlating the instantaneous detector output with the position of the flying-spot beam at that instant of time. In a corresponding "fanbeam" system an entire line is illuminated at once and individual pixels along the line are acquired either by a large number of discrete detectors arranged along the line, or one or more detectors with positional sensitivity. The transmission detector may comprise scintillators optically coupled to photomultiplier tubes. This method is more efficient and less noisy than using a photodiode array. The resulting improvement in signal/noise allows equivalent images to be made at lower doses and with lower beam energies.

The described embodiments of the invention are intended to be merely exemplary and numerous variations and modifications will be apparent to those skilled in the art. All such variations and modifications are intended to be within the scope of the present invention as defined in the appended claims.

What is claimed is:

1. A device, for inspecting a cargo container with penetrating radiation, the device comprising:

a. a bed that is reversibly moveable along a direction having a horizontal component;

b. a source of penetrating radiation, mounted on the bed for providing a beam having a central axis, the central axis being predominantly horizontal;

c. a motorized drive for moving the bed in the first direction;

d. at least one scatter detector mounted on the bed, each scatter detector having a signal output;

so that, as the bed is moved forward and backward along the direction, the beam is caused to traverse the cargo container as the bed is moved and each scatter detector provides a signal for characterizing the cargo container and any contents of the cargo container.

2. A device according to claim 1, wherein the a source of penetrating radiation is characterized by a source axis adjustable over a range of angles about the horizontal.

3. A device according to claim 1, further including a remotely operated actuator for selling a desired x-ray beam angle.

4. A device according to claim 1, further including an interlock for disabling the source of penetrating radiation unless the bed is in motion.

5. A device according to claim 1, wherein the scatter detector is a backscatter detector.

6. A device according to claim 1, wherein the beam is a pencil beam scanned repeatedly about an axis orthogonal to the source axis.

7. A method for producing an x-ray scatter image of a cargo container, the method comprising:

(a) providing a device having:

(i) a bed reversibly moveable along a horizontal direction;

(ii) a source of penetrating radiation, mounted on the bed, for providing a beam characterized by an adjustable beam axis;

(iii) a motorized drive for moving the bed in the first direction; and (iv) at least one scatter detector mounted on the bed and having a signal output;

(b) using the motorized drive to move the device past the cargo container so as to cause any contents of the cargo container to be scanned by the beam; and (c) processing (he signal from the signal output of the scatter detector as the bed is moved forward and backward along the horizontal direction to form an image of the contents of the cargo container.

*8. A device, for inspecting a cargo container with penetrating radiation, the device comprising:*

*a. a self-propelled vehicle moveable along a direction having a horizontal component;*

*b. a source of penetrating radiation, coupled to the self-propelled vehicle for providing a beam having a central axis, the central axis being predominantly horizontal;*

*c. a beam stop for absorbing the beam of penetrating radiation after traversal of the object; and*

*d. at least one scatter detector mounted on the self-propelled vehicle, each scatter detector having a signal output;*

*so that, as the self-propelled vehicle is moved along the direction, the beam is caused to traverse the cargo container as the self-propelled vehicle is moved and each scatter detector provides a signal for characterizing the cargo container and any contents of the cargo container.*

*9. A device according to claim 8, wherein the source of penetrating radiation is characterized by a source axis adjustable over a range of angles about the horizontal.*

*10. A device according to claim 8, further including a remotely operated actuator for setting a desired x-ray beam angle.*

*11. A device according to claim 8, further including an interlock for disabling the source of penetrating radiation unless the self-propelled vehicle is in motion.*

*12. A device according to claim 8, wherein the scatter detector is a backscatter detector.*

*13. A device according to claim 8, wherein the beam is a pencil beam scanned repeatedly about an axis orthogonal to the source axis.*

*14. A method for producing an x-ray scatter image of a cargo container, the method comprising:*

*a. providing a device having:*

*i. a self-propelled vehicle reversibly moveable along a horizontal direction;*

*ii. a source of penetrating radiation, mounted on the self-propelled bed, for providing a beam characterized by an adjustable beam axis;*

*iii. a motorized drive for moving the self-propelled bed in the first direction; and*

*iv. at least one scatter detector mounted on the self-propelled bed and having a signal output;*

*b. using the motorized drive to move the device past the cargo container so as to cause any contents of the cargo container to be scanned by the beam; and*

*c. processing the signal from the signal output of the scatter detector as the self-propelled bed is moved forward and backward along the horizontal direction to form an image of the contents of the cargo container.*

* * * * *